United States Patent
Caglioti et al.

(10) Patent No.: US 11,141,081 B2
(45) Date of Patent: Oct. 12, 2021

(54) CHEMICAL-PHYSICAL SYSTEM FOR TREATING TINNITUS

(71) Applicant: TINNITECH LTD, London (GB)

(72) Inventors: Luciano Caglioti, Rome (IT); Gioacchino Di Leo, Rome (IT); Robert Giovanni Nistico', Rome (IT); Monica Lentini, Rome (IT); Lino Di Rienzo Businco, Rome (IT); Bruno Brandimarte, Nettuno (IT)

(73) Assignee: TINNITECH LTD, London (GB)

( * ) Notice: Subject to any disclaimer, the term of this patent is extended or adjusted under 35 U.S.C. 154(b) by 157 days.

(21) Appl. No.: 16/343,284

(22) PCT Filed: Nov. 6, 2017

(86) PCT No.: PCT/IB2017/056919
§ 371 (c)(1),
(2) Date: Apr. 18, 2019

(87) PCT Pub. No.: WO2018/087645
PCT Pub. Date: May 17, 2018

(65) Prior Publication Data
US 2019/0254573 A1    Aug. 22, 2019

(30) Foreign Application Priority Data
Nov. 8, 2016    (IT) .................. 102016000112285

(51) Int. Cl.
*A61B 5/12*    (2006.01)
*A61K 9/00*    (2006.01)
(Continued)

(52) U.S. Cl.
CPC ............ *A61B 5/128* (2013.01); *A61K 9/0014* (2013.01); *A61K 9/0053* (2013.01); *A61K 9/06* (2013.01);
(Continued)

(58) Field of Classification Search
CPC ........ A61B 5/128; A61N 2/002; A61N 2/006; A61N 2/02
See application file for complete search history.

(56) References Cited

FOREIGN PATENT DOCUMENTS

| CN | 102793543 A | 11/2012 |
|---|---|---|
| WO | 0021440 A1 | 4/2000 |

(Continued)

OTHER PUBLICATIONS

International Search Report and Written Opinion for Corresponding International Application No. PCT/IB2017/056919 (dated Apr. 19, 2018) (32 Pages).

*Primary Examiner* — Christine H Matthews
(74) *Attorney, Agent, or Firm* — Lucas & Mercanti, LLP

(57) ABSTRACT

An acoustic device is configured to diagnose and treat tinnitus. The device includes a wearable support in the form of a headset, a pair of acoustic emitter-receivers, a pair of electromagnetic stimulation elements, an acoustic signals generator and an electromagnetic signals generator. The acoustic emitter-receivers and the electromagnetic stimulation elements are all are placed on the wearable support. The acoustic signals generator, which generates a diagnosis acoustic signal and a treatment acoustic signal to the acoustic emitter-receivers, is arranged on or associated with the wearable support. The electromagnetic signals generator, which induces microelectric signals to the electromagnetic stimulation elements, is also arranged on or associated with the wearable support.

14 Claims, 3 Drawing Sheets

(51) Int. Cl.
   *A61K 9/06* (2006.01)
   *A61K 9/48* (2006.01)
   *A61K 33/00* (2006.01)
   *A61K 36/15* (2006.01)
   *A61K 36/328* (2006.01)
   *A61K 36/484* (2006.01)
   *A61K 36/9066* (2006.01)
   *A61N 2/00* (2006.01)
   *A61N 2/02* (2006.01)

(52) U.S. Cl.
   CPC ............ *A61K 9/4808* (2013.01); *A61K 33/00* (2013.01); *A61K 36/15* (2013.01); *A61K 36/328* (2013.01); *A61K 36/484* (2013.01); *A61K 36/9066* (2013.01); *A61N 2/002* (2013.01); *A61N 2/006* (2013.01); *A61N 2/02* (2013.01)

(56) References Cited

FOREIGN PATENT DOCUMENTS

| | | |
|---|---|---|
| WO | 2010039465 A2 | 4/2010 |
| WO | 2012168543 A1 | 12/2012 |

CHEMICAL-PHYSICAL SYSTEM FOR TREATING TINNITUS

CROSS-REFERENCE TO RELATED APPLICATIONS

This application is a 371 of PCT/IB2017/056919, filed Nov. 6, 2017 which claims the benefit of Italian Patent Application No. 102016000112285, filed Nov. 8, 2016.

TECHNICAL FIELD OF THE INVENTION

The present invention relates to a device, to a topical composition, in particular in oily form, and to a capsule to be ingested for the treatment of tinnitus, also proposing a new therapeutic method. The invention also relates to a treatment kit comprising said device, topical composition and capsule.

BACKGROUND

The term tinnitus indicates the condition wherein a noise is perceived in one or both ears or in the head, although no sound is heard from the outside. Tinnitus can be defined as a "perception of sounds in the absence of physiological stimulation of the ear acoustic labyrinth" and is caused by the abnormal stress of any area of the acoustic path, from the spiral to the central cerebral areas located in the cortex.

Tinnitus is, therefore, completely different from other noises that can be generated in the blood vessels, in the Eustachian tube, in the muscles or in the temporomandibular joint, and which are transmitted through the skull bones. These noises can naturally stimulate the ear and be perceived by people other than the person who suffers from them. For this reason, these types of "sounds" are defined as objective tinnitus, whereas real tinnitus, called subjective tinnitus, can only be heard by the person who suffers from them.

Subjective tinnitus has mostly high-pitched tones and are often accompanied by hypoacusia (hearing loss). With the audiometric examination, it is possible to determine the frequency and intensity of a tinnitus (acufenometry). It is interesting to note that the volume of tinnitus, when measured with laboratory instruments, is not related to the severity of tinnitus perceived by the same patients.

Tinnitus has different characteristics depending on the patient. For example, some people perceive hearing disturbance only immediately after exposure to very loud noises, such as after a concert. Other people, on the other hand, say they hear a faint noise whenever they pay attention, but most of them cannot distinguish the noise from other environmental sounds.

Tinnitus is a symptom of a disease that can affect the ear (otogenic cause) or the whole organism (tinnitus by extraotogenic cause).

The many causes that can cause tinnitus, many of which are difficult to diagnose, make complex to diagnose and to cure the symptom, on the basis of which however it seems almost established that there is a neuronal hyperexcitation.

Therapeutic alternatives have been proposed and are still in use, each of which can give good results in individual cases.

Medical therapy is based on the use of vasodilators, anxiolytics and antidepressants (amitriptyline), herbal medicines (e.g. *Ginkgo biloba* extracts) or supplements.

Surgical therapy is based on very invasive measures, to be reserved for the most serious cases, which deprive the patient of the hearing on the tinnitus side.

Physical therapy is based on getting the patient used to listen to relaxing sounds (sound-therapy) and on to the use of particular acoustic prostheses, such as masks, which can interfere with the perception of tinnitus by supplying specific sounds.

In selected cases, hyperbaric oxygen therapy, which occurs in decompression chambers and is intended to oxygenate and revitalize inner ear cells, has been successfully used.

From a nutritional standpoint, foods that are likely to cause neuronal hyperexcitation are generally not recommended. Good therapeutic effects appear to be related to:
  protein-based diets by eliminating glycids and carbohydrates (metabolic ketosis),
  diets providing for the elimination of foods that can stimulate the release of histamine (eg salmon and tuna),
  diets based on taurine and glycine (inhibit neurons),
  purine diets (green vegetables, non-alcoholic beer, allopurinol).

However, despite tinnitus being an extremely widespread disorder and with a noteworthy social impact, truly effective and versatile technical systems and therapies have not yet been identified, particularly modulating the needs of the specific patient.

BRIEF DESCRIPTION OF THE INVENTION

The technical problem placed and solved by the present invention is therefore to provide an integrated therapeutic system, in particular based on the use of a technical device and a substance administration, preferably in combination with each other, capable of solving the above-mentioned drawbacks with reference to the known technique.

Said problem is solved by a device according to claim 1, a composition for oral administration according to claim 16 or 22, a composition for otological administration according to claim 25 and by a kit for use in the treatment of tinnitus according to claim 30 or 31.

Additional preferred features of the present invention are defined in the depending claims.

In the present context, "acoustic signal" is intended to mean a simple or complex combination of sound waves or sound of any duration.

The invention is based on an integrated therapeutic method for the treatment of tinnitus (tinnitus). This method involves the administration of:
  selected oral and topical functional-regulatory substances;
  sounds, by means of a dedicated technical device;
  quantized low frequency (ultrasonic) electromagnetic waves, preferably using the same technical device as mentioned above.

In particular, said method preferably comprises a biochemical step which involves administering medical droplets into the ear through the external canal and gastroresistant oral capsules, advantageously according to a predetermined dosage and posology for synergizing the various active ingredients, with the latter ones preferably being natural.

As mentioned above, the method further comprises an analytical/suppling step of administering sounds and electromagnetic waves, preferably using the same dedicated technical device.

Preferably, such device comprises a "headphone" dispenser and a programmable control unit that allows the operator (ENT specialist or audiometrician) or the patient to customize the treatment to better adapt to the peculiarities of the disease and to the actual therapeutic needs of the patient.

In its preferred embodiment, the proposed method involves the integration of four distinct therapeutic interventions (sounds, electromagnetic waves, a topical/otological substance and an oral substance).

Other advantages, together with the features and the use modes of the present invention will result evident from the following detailed description of preferred embodiments thereof, shown by way of example and not for limitative purpose.

BRIEF DESCRIPTION OF THE FIGURES

The drawings shown in the enclosed figures will be referred to, wherein.

DETAILED DESCRIPTION OF PREFERRED EMBODIMENTS

Figure 1:
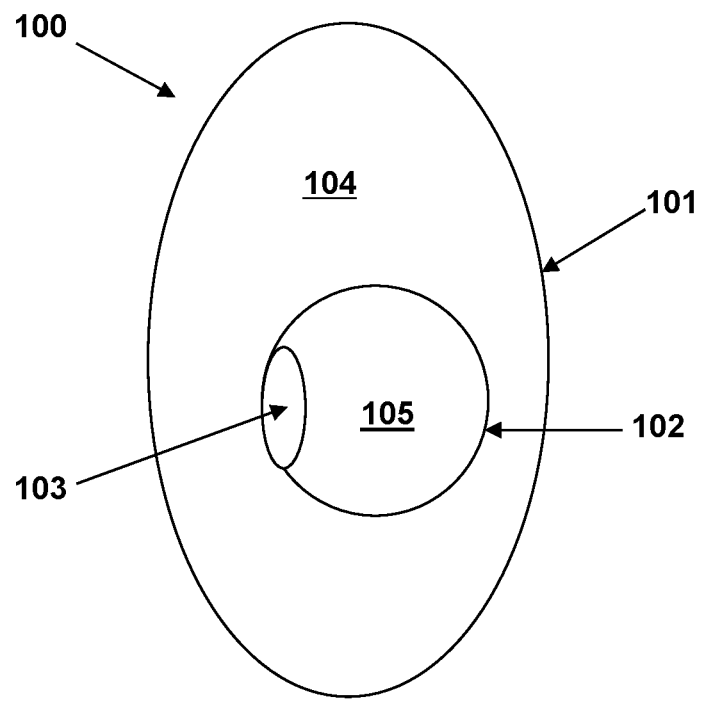
FIG. 1 shows a schematic partially-transparent representation of a composition of a biphasic capsule formulation for oral administration according to a preferred embodiment of the present invention.

Referring initially to FIG. 1, a gastro-resistant capsule according to a preferred embodiment of the invention is generally denoted by 100. Capsule 100 is configured for oral administration.

The capsule 100 has a gastro-resistant double-shell casing, comprising in particular a first gastro-resistant casing 101 which receives inside a second gastro-resistant casing 102. Between the two casings 101 and 102 is also interposed, particularly immediately applied on the second casing 102, a protective layer 103, preferably silica. The latter is configured to further "seal" the content of the inner casing 102, providing an additional barrier to the gastric pH. The two shells 101 and 102, thus, each define a respective internal compartment for receiving a relative active substance and said compartments do not communicate each other.

The double casing structure described above allows to receive a double active substance, in particular a first substance 104 in the first casing 101 and a second substance 105 in the second casing 102, allowing a selected release of a substance at a time. In other words, the first active substance 104 is released at a first proximal section of the intestine, with the dissolution of the first casing 101. The second active substance 105 is released at a second distal proximal section of the intestine, with the dissolution of the intestine protective layer 103 and second casing 102.

In other words, gastro-resistant casing 101 and 102 are configured to protect its content from hostile conditions that are faced in the metabolic pathway, especially in the strongly acidic stomach tract. Preferably, the two casings are both of the gastro-resistant type.

More specifically, the casing 101 and 102 are configured to release the active substance 104 at the area of the tenio-duodenic enteric tract and the active substance 105 in the following (duodenum-deep) tract.

Accordingly, it will be understood that the capsule structure 100 allows a selective release and a complete absorption of the single active substances according to the chemical-structural nature of their molecules.

Preferably, the first active substance 104 is in the form of a dry extract and the second active substance 105 is in the form of an oily solution.

In particular, in the present preferred embodiment, the first active substance 104 is a standardized and titrated extract in curcuminoids (preferably 95%), in particular obtained from Curcuma longa rhizomes in the form of a phytosomal extract to increase its overall bioavailability.

Curcuma has regenerating and protective action on neurons and powerful anti-inflammatory activity, as it reduces the synthesis of pro-inflammatory eicosanoids by inhibiting type 2 (COX2) and lipoxygenase (LO) cyclooxygenase. Type 2 cyclooxygenase, inducible and nonconstitutional enzyme such instead as COX1, synthesizes prostaglandins and thrombosans of Series 2, while the lipoxygenase synthesizes leukotrienes of Series 4.

According to a preferred embodiment of the invention, along with said curcuminous extract, low-dose Lithium Carbonate is envisaged to enhance the protective action on neurons and the stimulation of local stem cells.

According to a preferred embodiment, the second active substance 105 is an oily extract of Commiphora myrrha (Mirra), a gum resin obtained from its bark, with its strong analgesic properties due to the presence of sesquiterpenes, capable of activating the opioid receptors (with a pharmacological action generally equal to $1/10$ of morphine).

The aforementioned natural substances perform a functional-rebalancing activity, which is able to restore the homeostasis of auditory function altered by the presence of tinnitus disorder.

According to one embodiment, the concentration of curcuminoids in the composition will be between 150 mg and 450 mg, preferably between 200 mg and 300 mg, while the concentration of lithium carbonate will be between 0.5 mg and 5 mg, preferably between 1 mg and 2 mg and/or the oily extract of Commiphora myrrha (Mirra) will be comprised between 20 mg and 200 mg, preferably between 70 mg and 150 mg. To Mirra oil may be added from a minimum of 2% to a maximum of 10% of oleic acid as a functional excipient.

Preferably, the administration dose of capsule 100 is "bis-in-die" type (two per day).

According to alternative embodiments, the compositions for oral use will be in any of the following formulations: tablet, pill, powder, sustained release formulations, solution, suspension.

The capsules can be prepared, for example, by filling gelatin enclosures with the above-mentioned compounds. Lubricants and glides such as colloidal silica, talc, magnesium stearate, calcium stearate, or solid polyethylene glycol may be added to the mixture before the filling action. A disintegrating or solubilizing agent may be added to improve the availability of the drug when the capsule is ingested.

In addition, when desired or necessary, carries, binders, lubricants, disintegrating agents, dyeing agents may also be incorporated into the compositions for oral use. Suitable binders comprise, for example, starch, gelatin, natural sugars such as glucose or beta lactose, such as softeners, natural and synthetic gums such as acacia, tragacanth or sodium alginate, carboxymethyl cellulose, polyethylene glycols, waxes and the like. The lubricants used in these forms include sodium oleate, sodium stearate, magnesium stearate, sodium benzoate, sodium acetate, sodium chloride, and the like. Disintegrants include, for example, starch, methylcellulose, agar, bentonite, xanthan gum, and the like. The tablets are made, for example, by preparing a powder mixture, such as granulated or semi-finished, by adding a lubricant and a disintegrant and pressed into tablets. A powder blend is prepared by mixing the blended compound appropriately with a diluent or base as described above and, optionally, with a binder such as carboxymethylcellulose, a gelatin alginate or polyvinylpyrrolidone, a retardant for solutions such as paraffin, an accelerator of resorption such as a quaternary salt and/or an absorption agent such as bentonite, cauline or calcium diphosphate. The powder mixture can be granulated by wetting it with a binder such as a syrup, starch paste, acadia mucilage or cellulosic or polymeric materials solutions and forcing it through a partition. As an alternative to granulation, the powder blend can be passed through the tablet and the result is semi-processed grain-bound imperfect form. The granules can be lubricated to prevent sticking to the molds forming the tablets by adding stearic acid, stearate salt, or mineral oil.

The composition suitable for oral administration in the form of a tablet or capsule may comprise one or more pharmaceutically acceptable carriers and/or excipients suitable for the preparation of oral formulations. Examples of such carriers include lactose and cellulose. The tablet may or may also contain one or more pharmaceutically acceptable excipients, for example binders, lubricants such as magnesium stearate, and/or disintegrants.

A pharmaceutical composition suitable for oral administration in the form of a capsule can be prepared using encapsulation procedure. For example, pellets containing the active ingredient can be prepared using a suitable pharmaceutically acceptable carrier and then placed in a hard gelatin capsule. Alternatively, a dispersion or suspension may be prepared using any suitable pharmaceutically acceptable vehicle, for example an aqueous rubber or an oil, and the dispersion or suspension can then be immersed in a soft gelatine capsule.

Liquids for oral use such as solutions, syrups and elixirs may be prepared in the form of a discharging unit so that a given quantity contains a predetermined quantity of the above-mentioned compounds. The syrups can be prepared by dissolving the compounds in a suitably flavoured aqueous solution while the elixirs are prepared by the use of a non-toxic alcoholic vehicle. Suspensions can be formulated by dispersing the compound in a non-toxic carrier. Solubilizers and emulsifiers such as isostearyl alcohol ethoxylates and polyoxyethylene sorbitol ethers, preservatives, flavours such as peppermint oil or saccharin or other artificial sweeteners and the like can also be added. A liquid formulation will generally consist of a suspension or solution of the above-mentioned compounds in one or more suitable pharmaceutically acceptable liquid carriers, for example an aqueous solvent such as water, ethanol or glycerol, or a non-aqueous solvent such as polyethylene glycol or an oil. The formulation may also contain a suspension, preservative, flavouring and/or colouring agent.

According to another aspect of the invention, a composition suitable for otological administration is provided, thus for topical administration through the outer ear canal, preferably for a conjunct therapeutic use with capsule 100.

The composition for otological administration preferably comprises, in combination, one or more of the following substances:

an extract of *Glycyrrhiza glabra* standardized and titrated in 18-beta glycyrrretic acid in phytosomial form to increase its bioavailability (best dispersibility, longer duration of action and achievement of tissue levels ideal for anti-inflammatory, anti-irritative, anti-inflammatory activities—cortison-like effect with minimal side effects);

a sea *Pinus* bark extract, preferably a specific *Pinus marittimo* of the Bay of Biscay (France), standardized and titrated in Pycnogenolo, adapted to improve arteriovenous circulation, responsible for a greater supply of oxygen and nutrients, capable of rebalance the altered metabolism of cilia responsible for the tinnitus phenomenon;

Lithium carbonate in low-dose mode suitable for performing positive and stimulating action on the ear stem cells, neuroprotective action on auditory sensory neurons, as well as potentiating the antioxidant activity of the system.

Preferably, such substances are solubilized in a diethylene glycol monoethylether solution and almond oil or jojoba oil with the possible addition of oleic acid to improve the rheological aspect of the solution, which has the dual function of allowing a more effective solubilization of water-insoluble active substances, but also to exercise the very important role of "absorption promoter" namely substances that facilitate the crossing of active substances through the various existing biological membranes.

According to one embodiment, the concentration of 18-beta glycyrrretic acid is titrated at least between 40 and 98%, preferably 65 and 98% with respect to the total weight of the extract of *Glycyrrhiza glabra* and/or Pycnogenol is titrated at least 30% up to 75% compared to the total weight of the *Pinus marittimo* extract, preferably between 50 and 75%.

According to one embodiment, the concentration of *Glycyrrhiza glabra* extract will be between 0.5% and 5.0%, preferably between 1.5% to 3.5%, while the lithium carbonate concentration will be adjusted to give amount of Li ion comprised between 0.5 and 5 mg, preferably between 1 mg and 2.5; the *Pinus marittimo* bark extract will be comprised between 1% and 8%, preferably between 2 and 5%. The percentages are expressed as percentages of the total weight of the composition.

Preferably, also the otological solution dosage is "bis-in-die" (two per day), in the form of 10 gtt. per dose.

The composition may further comprise one or more carriers, diluents and/or excipients suitable for use in a composition for otological administration as known to the skilled person in the art.

The oral and topical compositions described above may be used in a method of treating tinnitus, preferably being used in association with one another by simultaneous or sequential administration preferably according to the dosage regimens described above.

According to one embodiment, the compositions are used in a method for the treatment of tinnitus comprising a step of administering sounds and electromagnetic waves, preferably such step of administering sounds and electromagnetic waves will be performed with the device according to the present invention.

According to one embodiment, the compositions will be used for the treatment of tinnitus associated with one or more of the following pathologies or pathological events: exostosis of the external acoustic meatus, acute and chronic otitis; tympanic-sclerosis, facial nerve paralysis, spasms of the ossicular chain muscles, tumors (tympanic paraganglioma), labyrinths, traumas and ear fractures, acute or chronic acoustic trauma, senile involutive labyrinth (due to aging), Menière disease (with dizziness), menieriform syndromes (with dizziness), herpes zoster oticus ("S. Antonio's ear fire"), otosclerosis (hereditary ear disease causing hypoacusia), neurological disorders: acoustic nerve and brain acoustic areas disorders: acoustic neuroma; toxic and infectious neuritis of the acoustic nerve; cranial traumas; intracranial pathological processes (plaque sclerosis, tumors); intracranial ischemic accidents (ictus, T.I.A.), intoxications, diabetes, gout (dysmetabolic diseases), liver failure, kidney failure, thyroid diseases, hypertension, hypotension, arteriosclerosis, anemia of various types, sympathetic stimulation: Neri-Barré-Lieoù syndrome (osteo-cervical osteoarthritis), Psychogenesis: auditory hallucinations.

The proposed posology for capsule 100 and for the otologic solution and their specific composition, in particular herbal ingredients in synergic formulation, allow the obtaining of potent synergies.

The daily double dosing ensures the achievement of suitable plasma peaks.

In addition, the otologic solution allows for simultaneous antioxidant, anti-inflammatory, neuronal, and topical stem cell acoustic stimulation actions.

Figure 2:
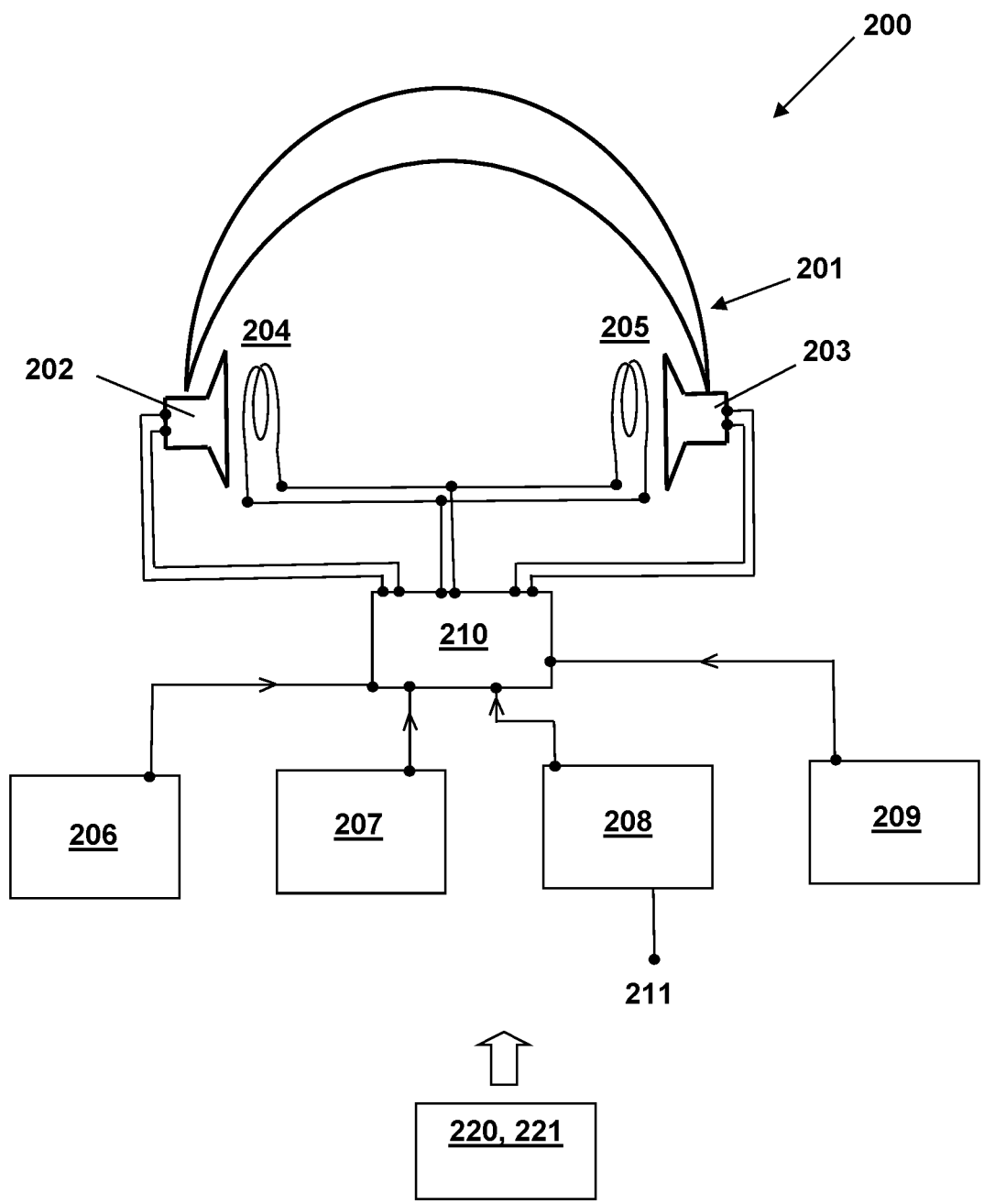
FIG. 2 shows a schematic representation of a technical device for the administration of sounds and electromagnetic waves according to a preferred embodiment of the invention, preferably intended for use in a same treatment with the capsule of FIG. 1 and with a pharmacological substance of oily type for topical use.
Figure 3:
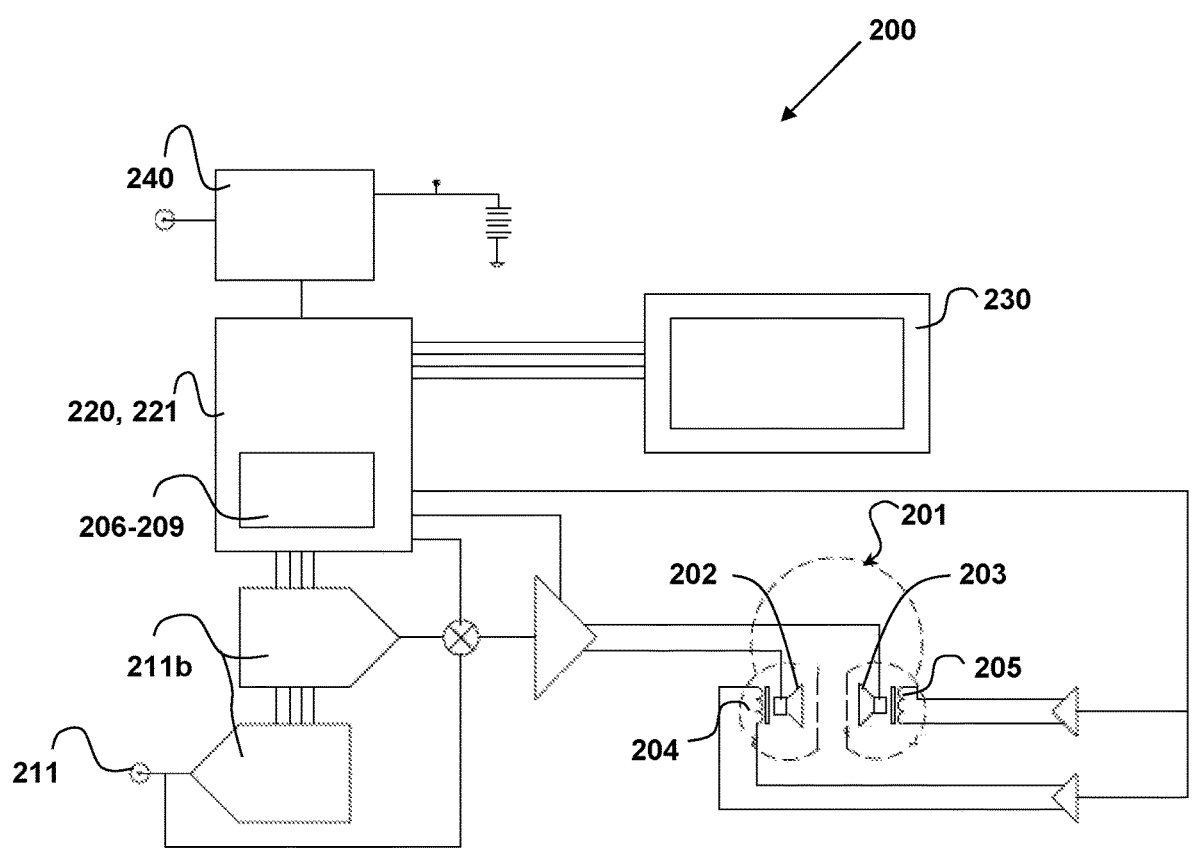
FIG. 3 shows a circuit design block diagram of a preferred embodiment of the acoustic/electromagnetic device shown in FIG. 2.

According to a further aspect of the invention, an acoustic and electromagnetic administration/stimulation device is provided. A preferred embodiment of this device is shown in FIGS. 2 and 3 and denoted as a whole with 200.

The device 200 comprises a wearable support 201, preferably in the form of a headset.

The device 200 further comprises a pair of dispensers, or emitters, acoustically connected to the support 201. In particular, a right emitter 202 and a left emitter 203 are provided, each providing acoustic signals at the respective auricle and to this end accordingly shaped. Emitters 202 and 203 may be connected to support 201 so as to be fixed or movable according to one or more degrees of freedom and possibly removably.

Each emitter 202, 203 is also a receiver and is further configured to receive an incoming acoustic signal, for example associated with a user's tinnitus disorder, and capable of transferring said incoming acoustic signal to units and components of the device that will be described in detail further in the present description.

In correspondence of or in proximity of each emitter/receiver 202, 203 is also provided a respective electromagnetic stimulation element, in particular an inductive solenoid 204, 205.

Preferably, each element 204, 205 comprises an enamelled copper wire winding, in particular with a cross-section within a range of 0.2 to 0.3 mm and for example with a number of coils ranging from 20 to 100, preferably in number equal to 50, such as to create an ultrasonic electromagnetic field suitable capable of generating electro-induction of microelectric signals in the inner area of the ear.

Each of said inductor solenoids 204, 205 preferably has a circular configuration, in particular with a maximum diameter of about 5 cm and is run by an adjustable current signal preferably comprised between 0.1 and 0.5 A.

As anticipated, the emitters/receivers 202 and 203 and the stimulation elements 204 and 205 are connected to further units of the device 200, in particular a signal mixing unit 210, which directly provides the acoustic and electrical signals respectively to said emitters/receivers and to said electromagnetic stimulation elements, which preferably also provides for their related power supply.

Mixing unit 210, in turn, is in communication, preferably bidirectional, with one or more further components of the device 200 described below.

In particular, an acoustic generator-resonator 206 is provided, which is configured to supply, by means of the mixing unit 210 and the emitters/receivers 202 and 203, an acoustic signal in the person's ear and to receive an indicative/representative resonance signal of the tinnitus. Said generator-resonator 206 is preferably provided with, or associated with, a control and regulation panel 230 for signals to be delivered, for example, made with touch-screen technology and shown in FIG. 3.

The generator-resonator 206, therefore, supplies a first acoustic signal, called diagnosis signal, which allows to create quantum bio-resonance in order to determine the frequency of the auditory disease and its intensity expressed in db. Preferably, the diagnosis acoustic signal is a variable frequency signal, so as to allow searching for subjective resonance, between 5 Hz (sub-sound) and 10 KHz (shrill whistle).

Preferably, there is also provided a processing unit 221 of the signals provided by the generator-resonator 206, which in turn controls an additional acoustic generator 207 so that the latter supplies a second acoustic signal, called treatment signal, capable of counteract the perception of tinnitus.

Both the diagnosis acoustic signal associated to the generator-resonator 206 that the treatment acoustic signal associated to the generator 207 are delivered by emitters 202 and 203 through the mixing unit 210.

In particular, the processing unit 221 stores and processes the data obtained with the generator-resonator 206 and uses them to program the treatment acoustic signal generator 207.

Generator 207, through the emitters 202 and 203, administers to the person said treatment acoustic signal which is, preferably, in the same form of the received resonance signal in terms of frequency and intensity, or a (partially) different acoustic signal.

For better clarity, a preferred interaction between the above components is described below as an example.

The generator-resonator 206 is configured to generate a first, preferably sinusoidal, acoustic signal, delivered by one or both emitters/receivers 202, 203.

Said first acoustic signal—or as mentioned diagnosis signal—is a variable frequency signal whose value can be displayed on a control and/or adjustment panel, denoted in FIG. 3 with the reference 230, and storable in the processing unit 221.

Specifically, through said panel 230, an operator may control the search for one or more specific frequencies associated with tinnitus disorder by adjusting for each frequency the amplitude (intensity) of the acoustic signal to be supplied.

The frequencies are preferably indicated in hertz (Hz), for example as a sequence of frequencies $F_1$-$F_2$-$F_3$- ... -$F_n$, and the corresponding intensities preferably expressed in db, for example $B_1$-$B_2$-$B_3$- ... -$B_n$, wherein n is equal to the number of frequencies (and intensities) searched and/or determined.

These values (that is both the frequencies/intensities associated with the search step and the frequencies/intensities subsequently determined) are displayed on panel 230 and the determined values are stored in the processing unit 221.

In response to the diagnosis acoustic signal so generated by the generator-resonator 206, the device 200—through the emitters/receivers 202, 203—is thus able to receive an incoming acoustic signal, namely a return acoustic signal associated with the tinnitus disorder.

The processing unit 221 is thus able to identify an acoustic resonance signal characterized by suitable data which is stored in the processing unit 221 itself.

In one embodiment, the device 200 is configured to identify and store preferably three main frequencies (and corresponding intensities) associated with the resonance acoustic signal obtained in response to the acoustic signal generated by the generator-resonator 206.

The processing unit 221 receives and processes data associated with the resonance acoustic signal, for example the frequencies $F_1$-$F_2$-$F_3$- . . . -$F_n$ and the corresponding intensities $B_1$-$B_2$-$B_3$- . . . -$B_n$, and controls the generator 207 to supply an acoustic treatment signal the emitters/receivers 202, 203.

Preferably, the treatment acoustic signal administered to the person and associated with the generator 207 is mixed with a secondary acoustic signal (or sub-signal), such as notes, music, noise.

For this purpose, the device 200 comprises an additional acoustic generator, that is the auxiliary generator denoted by the reference 208, in communication with the mixing unit 210.

Said auxiliary generator 208 is configured to supply said secondary acoustic signal, preferably sinusoidal and provided with a frequency of about 5 Hz (sub sound) and about 10 kHz (shrill whistle), which secondary signal may be suitably selected by an operator both in frequency and in intensity according to the type of application to be performed.

Thus, also the auxiliary acoustic generator 208 is preferably provided with, or associated with, a control and adjustment panel (for example the same control panel 230 shown in FIG. 3) for the secondary acoustic signals to be delivered. In preferred embodiments, the auxiliary acoustic generator 208 has internal storage means.

In an alternative operating mode, the auxiliary generator 208 is preferably provided with a control unit, which control unit is connected to said processing unit 221, said control unit being configured to receive data related to the resonance acoustic signal associated to tinnitus and as detected by the generator-resonator 206.

In preferred embodiments, the control unit associated to the auxiliary generator 208 is provided as a partition of said processing unit 221.

By way of example, and with reference to the above-mentioned example, the auxiliary generator 208 may use a sum of the signals associated to the tinnitus disease as identified by the generator-resonator 206, that is in consideration of the frequencies $F_1$-$F_2$-$F_3$- . . . -$F_n$ associated to the own resonance signal of the tinnitus and thus to generate a corresponding secondary composite acoustic signal.

In case, for example, during the diagnosis step, tinnitus is generated by a 150 Hz frequency signal, a 1500 Hz frequency signal, and a 2500 Hz frequency signal (each of which characterized by its intensity) the resulting composite secondary acoustic signal used by the auxiliary generator 208 will be a signal characterized by a fundamental frequency overlapped with the remaining two frequencies.

In terms of the calculation algorithm of said composite signal, the algorithm basically performs a frequency analysis of the signals associated to tinnitus.

With reference to the above frequencies (150 Hz, 1500 Hz and 2500 Hz), the three sinusoids in time domain are superimposed, each calculated with a function of the type: $f(t)$: $A \sin(\omega + a)$, wherein $A$=signal intensity, $\omega$=signal pulsation, $a$=initial phase of the signal.

Passing then in the frequency domain, the secondary composite acoustic signal will therefore be a summation of signals (e.g. through the use of the Fourier transform).

This secondary composite signal is then mixed with the signal supplied by the generator 207 through the mixing unit 210 and, subsequently, the so mixed signal is administered as a treatment signal to the person through the emitters/receivers 202, 203.

In further embodiments, the secondary acoustic signal may be pre-stored in the generator 208 or provided through an associated auxiliary input 211 that connects it to database or external generators of music signals, noise or other acoustic signals (music therapy).

In this latter case, auxiliary acoustic generator 208 is preferably configured as an acoustic amplifier of the acoustic signal provided with the auxiliary input 211.

Appropriate electronic components are therefore required to handle acoustic signals of different nature or origin, such as analogue/digital converters, multiplexers or the like, generically indicated by reference 211b in FIG. 3.

According to a preferred embodiment, the device 200 further comprises an additional electromagnetic generator 209, in particular an ultrasonic frequency electromagnetic generator, configured for generating an electromagnetic signal at an ultrasonic frequency, preferably at discrete values, such as for example an electromagnetic signal characterized by frequencies of about 20 kHz, about 25 kHz and about 30 kHz.

Said additional electromagnetic generator 209 is also preferably provided with, or associated with, a control and adjusting panel for the acoustic signals to be delivered, for example the same panel 230 mentioned above.

Accordingly, the operator can search, select, and store, for example, one or more appropriate frequencies (and corresponding intensity) of the ultrasonic signal associated to the operation of the additional generator 209.

Said ultrasonic signal, transduced electromagnetically, is then delivered solely to the electromagnetic stimulation elements 204, 205, preferably via a dedicated area of the mixing unit 210.

In a preferred embodiment, the device 200 also includes an additional control unit 220, preferably in bidirectional communication with all the units and components of the device itself and optionally integrated with the aforementioned unit 221.

In this way, the ultrasonic signal obtained by the generator 209 is sent to the electromagnetic stimulation elements 204 and 205 preferably via the control unit 220. The latter processes/transduces acoustic signals (in this case ultrasonic) and generates corresponding electrical signals to be delivered to the stimulation elements 204 and 205.

Stimulation elements 204, 205 generate electromagnetic signals configured of inducing microelectric signals in the acoustic nerve area causing a light hyperemia and interfering with the transmission of the disorder to the brain.

These electrical signals induced on the acoustic nerve allow the function to activate at a cellular level, through the delivery of athermal energy, ATP transformation in ADP with the relative oxygen demand (via microematic) and reducing the electrical space available to the disease signal on the electric nerve transmission.

Control units 220, 221 can be obtained as a common component, that is shared for the different generators, units and elements mentioned hereinbefore, or be formed by multiple control means associated with single units or generators.

Preferably, the control units 220, 221 or the above-mentioned control means are microprocessor type.

In addition, the units and generators above introduced, although described as structurally and/or functionally separated, can be incorporated into the same multifunction unit.

Still, as already partially mentioned, each of these components may include a dedicated control and/or adjustment panel, or one or more of said panels may be provided on a common support.

As mentioned above, the configuration of acoustic generators as proposed, in particular through the generator-resonator 206 and the mixing unit 210, allows to determine a quantum bio-resonance in order to determine the frequency and intensity of tinnitus.

Therefore, typically, in use, the diagnosis acoustic signal is determined on the base of tests performed on patient to obtain the resonance signal and hence the intensity and frequency of tinnitus. Once this determination has been made, the treatment signal to be delivered is processed, which may optionally be stored in generator 207, 208 and/or 209 and permanently used.

The characteristics of the treatment signal—in particular the frequency of the modulated signal and of the modulating signal for the electromagnetic portion of the stimulation—can be established in a first session of treatment by testing the patient's feeling of tinnitus noise reduction, for example firstly at 20 kHz, then at 25 kHz and then at 30 kHz. The best frequency can be chosen, which can also be confirmed in a second preliminary session.

The acoustic and/or electromagnetic signal given to the person respectively by the emitters/receivers 202, 203 and by the electromagnetic stimulation elements 204, 205 may have different characteristics with reference to the right and left auricle, or be administered at a single auricle, depending on the characteristics of the disease detected during the diagnosis step.

Advantageously, the device 200 as a whole—comprising emitters/receivers 202-203, stimulation elements 204-205 and generators and units 206-210 above mentioned—possibly with the exception of the control unit 220, 221, is provided in two versions, one of which is a studio device comprising the diagnostic features and a second one entirely portable and/or wearable, that is such generators and units are placed on the support 201 or on a different base applicable to the patient's body, said second version not being configured to allow a change to the programming.

The device 200 can be self-powered by batteries 240, possibly rechargeable, and/or be connectable to an external power source. Battery discharge may be signaled, for example, on control panel 230, to allow connection to the battery charger.

Preferably, the device 200 is not operative during the charging phase.

Additionally, the battery life is calculated so as to guarantee the autonomy of the device 200 for a duration of at least 10 cycles of treatment.

In summary, the physical part of the method develops its action in various synchronous phases with the administration of active substances taken both in capsules and introduced into the ear canal, according to main steps as follow.

Determination of the signal generating tinnitus by quantum bio-resonance method (to define either the frequency and the quantum intensity of the disease).

Administration to the person of acoustic signals related to the disease, mixed with others that can compress and reduce the transmission of the disease signal to the brain, preferably selected and stored in the medical office with the studio device and subsequently delivered at home (twice a day) for 60 days cycles.

Induction in the acoustic area of microelectric signal causing light hyperemia and that interferes with the transmission of the disease to the brain, preferably always delivered after been selected and stored in the medical office and then domiciliary for sixty days of cycles (twice a day).

It will be better understood, at this point, that the proposed system and methodology provide for the synchronized use of pharmacological substances, preferably of phytotherapeutic origin, with synchronous function for both gastrointestinal and local intake. These substances, with their anti-inflammatory and circulatory action, prepare the auditory organ and its transmission system to the targeted action of the physical means guided by the quantum bio-resonance phase. The overall therapeutic system is obviously synergistic, contrary to the methodologies currently in use that are applied separately and randomly as well as with much more limited and partial effectiveness.

Advantageously, in clinical practice, the methodology allowed by the invention is associated with a preliminary counseling phase that in particular probe all the possibilities and help the patient with in-depth explanations of the symptoms and possible therapies.

Preferably, the diagnosis is formulated by means of a specialist examination complemented by instrumental tests aimed to verify the auditory ear, in particular audiometry, acufenometry, impedenzometry, ABR, and other types of controls to diagnose secondary tinnitus to extra-otogenic causes: blood test, Ecg, Ecg and pressory Holter, Eco-doppler TSA and others.

According to a further aspect of the invention, there is provided a method for treating a patient with tinnitus disease comprising a step of administering to said patient the above-described oral and topical compositions and a further step of administering sounds and electromagnetic waves, preferably by means of the device described herein.

According to a preferred embodiment, the method of treatment comprises the steps indicated below.

Initially, the biphasic capsule is to be taken and the drops instilled that will be prolonged for a long time, for example 12/18 months. Preferably, the intake will follow this protocol: in the morning instill the drops into the auditory canal, e.g. before breakfast; then with the help of a cotton wool, close the outer ear canal to prevent regurgitation of the drops; at lunch time a biphasic capsule before lunch would be better, or if it is a senior patient already in treatment with other medicines even after the meal; in the evening before dinner, reinsert the drops with the same methodology and before going to sleep take the second biphasic capsule.

This rhythm of administration allows the synergy of active principles that, spaced in the various dosages, have pharmacokinetic times in tune to synergize.

After taking pharmacological principles, such as at least 3 or 4 days, a first session of control and programming will be organized as illustrated below.

With the generator 206, the frequencies and intensities of the resonances are sought (preferably from one to three main frequencies), singularly quantify the latter in db, to obtain on a control panel a correspondence like: $F_1$ (Hz), $B_1$ (db); $F_2$ (Hz), $B_2$ (db); and so on depending on the number of frequencies associated with the detected resonance signal.

With data so obtained, the generator 207 and optionally the generator 208 and/or 209 will be programmed.

For example, with the arithmetic average of $F_1$, $B_1$-$F_2$, $B_2$-[ ... ]-$F_n$, $B_n$ (automatically indicated by the control unit processor) will be programmed (preferably automatically by means of, for example, a "enter" button) the acoustic treatment signal emitted by generator 207 which, as said, may possibly be mixed with a secondary (sub-signal or external) acoustic signal generated by auxiliary generator 208 or provided with auxiliary input 211.

Through the electromagnetic stimulation elements 204, 205 of the headset 201, an electromagnetic signal will also be supplied to the person as transduced by a respective ultrasonic signal and preferably generated in succeeding frequencies of 20 KHz-25 KHz to 30 KHz, further modulated in amplitude with the acoustic signals obtained with the generator 207 and/or 208 and of amplitude equal to that one obtained in db with the generator 206.

After the measurement and verification and programming step above, the acoustic and electromagnetic signals will be delivered for 30 minutes. After that time, a check will be made for the condition of the disease.

At the end of the session and the check the patient will be assigned an automatic portable device designed to deliver as determined in the previous step and that will be used preferably in the evening for 30 minutes before bedtime and in the morning for 30 minutes.

After about three days from the preliminary session, a second test will be carried out with the same procedure to check the efficiency of the first programming and eventually adjusting the automatic programming of the device provided to the patient.

Subsequently, a control session will be performed after 30-60 days, preferably 60 days of treatment.

Preferably, the methodology is performed by two apparatus, a studio device for use in the two preliminary sessions and check sessions and a portable programmed one that will be given to the patient and used domiciliary but that cannot be modified in the programming by the patient himself.

Preferably, the device for domiciliary use is analogous to the study device but may not having the acoustic generator-resonator 206. In particular, the device for domiciliary use is programmable only by the operator of the office which provides to the latter a configuration as determined in the office session procedure.

Therefore, with regard to the device for domiciliary use, the (acoustic and/or electromagnetic) signals associated to generators 207, 208, 209 or to auxiliary input 211 will not be modified by the patient who will only be capable to switch the device on or off.

The device for domiciliary use is also preferably powered by rechargeable batteries via a power supply comparable to that of the study device and is equipped with means of signaling charging and cannot operate during the charging phase.

The lifetime of the device for domiciliary use is such as to guarantee an autonomy of at least 5 cycles of treatment.

Some applicative examples, for exemplifying and non-limitative purposes, are reported as follow.

EXAMPLES

Example 1—Preparation of the Composition for Oral Use

As a first step, we will weigh the right amount of Myrra Oil for a batch of small-seized capsules: then the gelled silica is added to "seal" the two edges of the capsules and prevent the Myrrh Oil out of the capsule;
upon completion of this operation, the capsules, now well closed, of small size will be deposited in the larger capsules and, therefore, will be added to all the capsules provided for the batch, a mixture, firstly prepared and weighed, in specific ratios between the two components, as in the examples described above, well amalgamated, according to the method of gradual dilution, of powder of phytosomial Curcuma longa and of Lithium Carbonate; addition of excipients is planned and what else to improve the organoleptic aspects of the active ingredients and their perfect mixing (as already described above).

At this point a dedicated machine will close the larger capsule: in this way the two capsules will be ready for administration.

Example 2—Preparation of the Composition for Topical Use

Functional substances for the preparation of the oily solution will be:
phytosomial *Glycirrhiza glabra* powder in the quantity given in the description.
Dry extract of *Pinus marittimus* titrated in Pycnogenol (in percentage as described in the description);
Lithium Carbonate in low-dose powder mode in the quantity described above.
To the individual powders after appropriate weighing and mixing, an Almond Oil and/or Jojoba Oil solution (strictly prepared according to the F.U. method or purchased as complying with it) is added: it will wait for the solution to be clear (otherwise it may be added Oleic acid or ethoxydiglycol by addition of a Polyglyceryl-3 Polyricinoleate emulsifier in a quantity as described in the proceeding examples, using appropriate mixing techniques (according to normal procedures in use in all laboratories and production facilities); add preservatives and anything else to a better product stability, the container will be in dark glass or dark plastic for ultraviolet rays protection and the dispenser appropriate for otological use, that is it can easily dispense 10 gtt as provided; the bottle will be chosen on the basis of a suitable use for a month-long therapy.

In an alternative preparation, the composition for topical use is prepared as follows.

The following substances: *Glycyrrhiza* glaze standardized extract and titrated in 18-Beta glicirretic acid in phytosomial form, Maritime *Pinus* Bark Extract and Lithium Orotate, are solubilized in an APV solution (diethyleneglycol monoethylether better known as Trascutol P). The diethyleneglycol monoethylether has the dual function of allowing more effective solubilization of water-insoluble active substances (it is possible to use hydrophilic surfactants soluble substances—to ensure the total solubility of the used powders), but also to exercise the very important role of "Absorption promoter" that is substances that facilitate the crossing of active ingredients through the various existing biological membranes (first enhancer); we also added an oleic acid solution, both to improve the rheology of the solution and to increase the passage through the biological membranes of the active ingredients used (second enhancer). The major solvent is Jojoba Oil F.U. which has the lowest density index and therefore better organoleptic behaviors than other commercially available oils (see Almond Oil, Olive Oil, etc.). For a volume pack of 30 ml, 3.75 mg of Lithium Orotate will be used equal to one mg. of metal ion.

Example 3—Clinical Data Demonstrating the Claimed Therapeutic Effect

It was considered to preliminary perform a study on a small but significant number of patients all with tinnitus of unspecified origin. For preliminary sessions, one of the inventors the otorino medical office has been used using a prototype apparatus, while the capsules and oily substance has been prepared in the drug laboratory of another inventor. All patients treated between the ages of 25 and 60 were affected by real diseases between a strong buzz to a hiss around 3000 Hz of high intensity such as to trouble or, actually, impede rest. The protocol was followed according to a preferred embodiment of the present invention that is after the first pharmacological components were taken for 3 days, the first preliminary session with parameter determination was made, then patients were assigned a portable device used for 30 minutes in the evening before sleeping. Subsequently after another 3 days a check session was held that confirmed the program settings made in the first session. Both pharmacological and physical treatment continued for 45 days and then the first check was performed and an improvement with symptom reduction was found between the eighty and ninety percent. Continuing for another 45 days, a new check shown the improvement was stabilized. Obviously, we will proceed in the treatment and check until reaching 12/18 months from the beginning of the treatment. It is expected to broaden experimenting with respect to another 30 patients operating in the university framework.

The present invention has been so far described by referring to preferred embodiments thereof. It is to be meant that other embodiments could be envisaged, belonging to the same inventive core as defined in the protection scope of the herebelow reported claims.

The invention claimed is:

1. An acoustic device configured for a diagnosis and treatment of tinnitus, said device comprising:
   a wearable support comprising a headset;
   a pair of acoustic emitter-receivers each placed on said wearable support so as to be positioned, in use, at a respective auricle of a patient;
   a pair of electromagnetic stimulation elements each placed on said wearable support in such a way as to induce, in use, microelectric signals in correspondence or proximity of a respective auricle of a patient;
   an acoustic signals generator, arranged on or associated with said wearable support and configured for generating a diagnosis acoustic signal and a treatment acoustic signal, said acoustic signals generator being configured for supplying a variable frequency acoustic signal; and
   an electromagnetic signals generator, arranged on or associated with said wearable support and configured for inducing microelectric signals in an auditory nerve area through said electromagnetic stimulation elements,
   wherein
   said acoustic signals generator is configured to supply said diagnosis acoustic signal through said acoustic emitter-receivers, to receive an acoustic resonance return signal indicative of tinnitus and to generate a corresponding treatment acoustic signal, and
   said electromagnetic signals generator being a generator of electromagnetic signals at ultrasonic frequency configured for generating said microelectric signals to be induced as a function of said diagnosis acoustic signal, said acoustic resonance signal and/or said treatment acoustic signal.

2. An acoustic device according to claim 1, further comprising a signal mixing unit configured for receiving two or more acoustic input signals from said acoustic signals generator and/or said electromagnetic signals generator and for suppling as output said treatment signal.

3. An acoustic device according to claim 1, wherein each acoustic emitter-receiver is configured in such a way as to supply, in a diagnosis stage, said diagnosis acoustic signal at the respective auricle and to receive said resonance return signal.

4. An acoustic device according to claim 1, further comprising a unit for determining a frequency and/or intensity of said acoustic resonance return signal, said unit being associated with a control unit, said acoustic signals generator and/or to said electromagnetic signals generator.

5. An acoustic device according to claim 1, wherein each acoustic emitter-receiver is configured in such a way as to supply, at a treatment stage, said treatment acoustic signal.

6. An acoustic device according to claim 1, wherein said acoustic signals generator comprises an auxiliary acoustic generator configured for generating sounds with a frequency between a sub-sound band and that of ultrasound.

7. An acoustic device according to claim 6, wherein said auxiliary acoustic generator is configured for generating a composite signal based on a sum of signals with frequencies $(F_1\text{-}F_2\text{-}F_3\text{- } \ldots \text{ -}F_n)$ associated with the acoustic resonance return signal.

8. An acoustic device according to claim 1, wherein said electromagnetic signals generator comprises an additional electromagnetic generator configured for generating an ultrasonic signal.

9. An acoustic device according to claim 1, wherein said acoustic signals generator and/or said electromagnetic signals generator comprises means for storing signals.

10. An acoustic device according to claim 1, wherein said acoustic signals generator and/or said electromagnetic signals generator is configured for a connection with a signal database external to the device.

11. An acoustic device according to claim 1, comprising a control panel operable by a user to select a program for delivering a diagnosis and/or treatment signal.

12. An acoustic device according to claim 1, wherein said acoustic signals generator and/or said electromagnetic signals generator comprises a source of autonomous power supply.

13. An acoustic device according to claim 8, wherein the electromagnetic signals are characterized by frequencies of about 20 kHz, about 25 kHz and about 30 kHz.

14. An acoustic device according to claim 1, wherein said electromagnetic signals generator comprises an additional electromagnetic generator configured for generating an ultrasonic signal at discrete values.

* * * * *